(12) United States Patent
Schmidt-Richberg et al.

(10) Patent No.: US 11,334,992 B2
(45) Date of Patent: May 17, 2022

(54) COMPUTER-IMPLEMENTED METHOD TO INCREASE THE ACCURACY OF MACHINE LEARNING MODELS FOR MEDICAL IMAGE PROCESSING

(71) Applicant: KONINKLIJKE PHILIPS N.V., Eindhoven (NL)

(72) Inventors: Alexander Schmidt-Richberg, Hamburg (DE); Martin Bergtholdt, Hamburg (DE); Tobias Klinder, Uelzen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 164 days.

(21) Appl. No.: 16/789,489

(22) Filed: Feb. 13, 2020

(65) Prior Publication Data
US 2020/0265579 A1 Aug. 20, 2020

(30) Foreign Application Priority Data

Feb. 14, 2019 (EP) .................................... 19157254

(51) Int. Cl.
*G06T 7/00* (2017.01)
*G06K 9/62* (2022.01)
(Continued)

(52) U.S. Cl.
CPC .......... *G06T 7/0012* (2013.01); *G06K 9/6215* (2013.01); *G06K 9/6267* (2013.01); *G06N 20/00* (2019.01); *G06T 7/10* (2017.01); *G06T 2207/10081* (2013.01); *G06T 2207/10088* (2013.01); *G06T 2207/10116* (2013.01); *G06T 2207/20081* (2013.01)

(58) Field of Classification Search
CPC ..................... G06T 7/0012; G06T 7/10; G06T 2207/10081; G06T 2207/10088; G06T 2207/10116; G06T 2207/20081; G06N 20/00; G06K 9/6215; G06K 9/6267; G16H 50/20; G16H 30/40
See application file for complete search history.

(56) References Cited

U.S. PATENT DOCUMENTS

| 6,760,468 B1 | 7/2004 | Yeh et al. |
| 2009/0052768 A1 | 2/2009 | Zhao |

(Continued)

OTHER PUBLICATIONS

Shin, H. et al., "Learning to Read Chest X-Rays: Recurrent Neural Cascade Model for Automated Image Annotation", 2016 IEEE Conference on Computer Vision and Pattern Recognition.

(Continued)

*Primary Examiner* — Siamak Harandi
(74) *Attorney, Agent, or Firm* — Micah-Shalom Kesselman

(57) ABSTRACT

There is provided a computer implemented method (200) for medical image processing. The method comprises providing (202) a database of medical images and providing (204) an initial machine learning model which is trained for segmenting or classifying a medical feature in the medical images. The method also comprises extracting (206) a subset of medical images from the database based on a similarity score of the medical images and training (208) the machine learning model using the extracted subset of medical images in order to provide a refined machine learning model.

11 Claims, 5 Drawing Sheets

(51) Int. Cl.
    *G06T 7/10*     (2017.01)
    *G06N 20/00*     (2019.01)

(56) References Cited

U.S. PATENT DOCUMENTS

| | | |
|---|---|---|
| 2009/0138432 A1 | 5/2009 | Agnihotri et al. |
| 2010/0281037 A1 | 11/2010 | Agnihotri et al. |
| 2017/0083793 A1* | 3/2017 | Shie ................ G06T 7/0014 |
| 2019/0027252 A1* | 1/2019 | Calhoun .......... G06K 9/6247 |

OTHER PUBLICATIONS

Shen, D. et al., "Deep Learning in Medical Image Analysis", Annu. Rev. Biomed. Eng. 2017. 19:221-48.

Brosch, T.; Saalbach, A.: Foveal fully convolutional nets for multi-organ segmentation. Proc. SPIE, 105740U, 2018.

Zeitler, M. D.; Fergus, R.: Visualizing and Understanding Convolutional Networks. Proc. ECCV, 2014.

Pan, S. J.; Yang, Q.: A survey on transfer learning. IEEE Trans Knowl Data Eng, 22(10), 1345-1359, 2009.

Hwang, K. Hi; Lee, H.; Choi, D.: Medical Image Retrieval: Past and Present. Healthc Inform Res, 18(1), 3-9, 2012.

Wolz, R. et al.: LEAP: Learning embeddings for atlas propagation. NeuroImage, 49(2), 1316-1325, 2010.

Kingma, D. P. and Welling, M.: Auto-encoding variational bayes. International Conference on Learning Representations (ICLR), 2014.

\* cited by examiner

COMPUTER-IMPLEMENTED METHOD TO INCREASE THE ACCURACY OF MACHINE LEARNING MODELS FOR MEDICAL IMAGE PROCESSING

CROSS-REFERENCE TO PRIOR APPLICATIONS

This application claims the benefit of European Patent Application No. 19157254.4, filed on 14 Feb. 2019. This application is hereby incorporated by reference herein.

FIELD OF THE INVENTION

The disclosure relates to providing machine learning models for processing medical images.

BACKGROUND OF THE INVENTION

The general background of the present disclosure is the use of machine learning models for medical image segmentation and/or medical image classification e.g. for distinguishing between benign and malignant structures, which may be used for identification of various pathological conditions based on an acquired medical image. Therein, machine learning models are usually trained using supervised learning, where the network is trained for a specific task using numerous representative images with corresponding ground-truth delineations of the structure to be segmented. In this way, the network is able to learn image features that are relevant for the specific segmentation task. Typically, those features range from very abstract features like edges or corners in the first layers to complex patterns in later layers of the network.

However, for the task of segmentation of any medical features, such as pathological features, physiological features or the like, finding universally relevant features is particularly challenging, because the appearance of medical features may be very diverse. For example, lung nodules tend to vary considerably in size, density (solid, part-solid, non-solid/ground glass opacity), and border definition (spiculated, lobulated, ill-defined, or smooth). For an accurate segmentation, it would thus be advantageous if a machine learning model could learn specific features for each different type. However, known machine learning models tend to only learn a general network based on large databases. As these general networks model the entire database, they lack accuracy to address distinct sub-tasks that are underrepresented.

Similarly, models for classification of medical images may be provided for classifying pathological conditions or the like, wherein machine learning models may be trained for a specific classification task such as e.g. distinguishing between benign and malignant lung nodules, and where the same problems occur regarding the lack of accuracy in distinct classification sub-tasks that are underrepresented in the general training database.

SUMMARY OF THE INVENTION

As described above, it is thus desirable to increase the accuracy of a machine learning model for feature segmentation of medical images or for feature classification of medical images, especially in cases where the appearance of pathological or physiological conditions may be very diverse so that a general machine learning model may not be able to identify each different type of medical feature with the required accuracy. In the present disclosure, the term "identification" is used as a general term covering both the task of segmenting a medical feature, i.e. of detecting the presence and the location and boundaries of a medical feature such as a pathological feature or a physiological feature in an image, as well as the task of classifying a medical feature, i.e. of evaluating a medical feature such as a pathological feature or a physiological feature according to a predetermined classification system.

According to a first aspect, a computer implemented method for medical image processing is provided. The method comprises providing a database of medical images and providing an initial machine learning model which is trained for segmenting or classifying a medical feature, such as e.g. a pathological or physiological feature, in the medical images. The method further comprises extracting a subset of medical images from the database based on a similarity score of the medical images, and training the machine learning model using the extracted subset of medical images in order to provide a refined machine learning model. Thus, the refined machine learning model has inherited the general capabilities for segmentation or classification of medical features (e.g. pathological or physiological features) of various different types and appearances by transfer learning, and is then trained further using a subset of medical images that are selected based on a similarity score. The refined machine learning model can thus deliver an accurate medical feature segmentation or an accurate medical feature classification for a particular type and appearance of a medical feature even if few training images are available for the specific condition, since the refined machine learning model inherits the characteristics of the general, initial machine learning model that can be trained on a wide range of medical images.

According to some embodiments, the method may further comprise acquiring a medical image that is to be processed. Therein, the step of extracting the subset of medical images from the database may be performed based on a similarity score between the acquired medical image and the extracted medical images. In this way, the extracted medical images may be selected based on their similarity to the acquired image. Thus, the refined medical image, which is trained using the selected subset of medical images, is particularly suitable for processing the acquired image.

According to some embodiments, the method may further comprise identifying a region of interest in the acquired medical image, and determining the similarity score based on the region of interest. In this way, it can be ensured that the similar images for retraining the machine learning model are selected based on characteristics of the medical feature to be segmented or classified, and not on artefacts regarding e.g. the specific scan size or region of the acquired medical image.

According to some embodiments, the method may further comprise segmenting or classifying a medical feature in the acquired medical image using the refined machine learning model. Thus, the refined machine learning model may be used to identify a specific medical feature in the acquired medical image.

According to some embodiments, the method may comprise extracting multiple subsets of medical images from the database based on a similarity score between the medical images of the database; acquiring a medical image, selecting one subset of the multiple extracted subsets of medical images based on a similarity score between the medical images in each of the extracted subsets and the acquired medical image, and segmenting or classifying a medical feature in the acquired medical image using the refined machine learning model which has been trained using the selected subset of medical images. Thus, for an acquired medical image, the most suitable refined machine learning model can be identified based on the similarity between the subset used for training the refined machine learning model and the acquired image. The identified refined machine learning model can then be used in order to provide an accurate segmentation or classification of a medical (e.g. pathological or physiological) condition in the acquired image.

According some embodiments, the initial machine learning model may be trained for feature segmentation or classification using the database of medical images. In this way, a general initial machine learning model is provided that is trained for medical feature segmentation or classification over a wide range of possible appearances and characteristics of the specific medical features that are to be detected, such as specific pathologies or specific physiological structures or the like that are to be detected.

According to some embodiments, the medical images may comprise any of computerized tomography (CT) scan images, X-ray images, magnetic resonance imaging (MRI) images or ultrasound images. Therein, the medical images may e.g. depict organs or parts thereof, such as lung nodules, or may be images of bone fractures, fetuses, or images of any other medical structures.

According to some embodiments, the similarity score may be determined based on a latent space representation of the medical images in the database. Thus, a cluster of similar medical images may be identified using the latent space grouping of the medical images in the database.

According to some embodiments, the similarity score may be based on content information of the medical images. Therein, the content information may comprise information relating to nodule type, size, degree of speculation, or the like.

According to some embodiments, the method may further comprise displaying the extracted subset of medical images. Thus, the subset of medical images used for training the refined machine learning model can be inspected by a clinician in order to verify that relevant training images have been used in the training process of the specific network.

According to a second aspect, a system for medical image processing is provided, comprising a memory storing a database of medical images and a processor. The processor is configured to provide an initial machine learning model which is trained for segmenting or classifying a medical feature in the medical images, extract a subset of medical images from the database based on a similarity score of the medical images, and train the machine learning model using the extracted subset of medical images in order to provide a refined machine learning model. Thus, the processor can provide additional training to the initial machine learning model, using a subset of the medical images which are selected based on a similarity score, in order to arrive at a refined machine learning model which can provide a highly accurate segmentation or classification of a medical feature for a specific task.

According to some embodiments, the processor may further be configured to acquire a medical image that is to be processed, and to process the medical image using the refined using the refined machine learning model in order to provide a processing result of the acquired medical image.

According to a third aspect, there is provided a computer program product comprising a computer readable medium. The computer readable medium has computer readable code embodied therein. The computer readable code is configured such that, on execution by a suitable computer or processor, the computer or processor is caused to perform the method described earlier.

Therein, as described above in conjunction with the various aspects and embodiments of the method, the refined machine learning model may have been trained in an online process, wherein a subset of medical images which are similar to the acquired medical image may have been selected for training the refined machine learning model, or the refined machine learning model may have been trained in an offline process, wherein multiple subsets of medical images may have been selected based on a similarity cluster analysis or the like of the medical images in the database, and the acquired image may be processed using a refined machine learning model which has been trained based on the subset that is most similar to the acquired image.

These and other aspects will be apparent from and elucidated with reference to the embodiment(s) described hereinafter.

BRIEF DESCRIPTION OF THE DRAWINGS

For a better understanding of the embodiments herein, and to show more clearly how they may be carried out, reference will now be made, by way of example only, to the accompanying drawings, in which.

DETAILED DESCRIPTION OF EMBODIMENTS

As described above, for medical images related to medical features (e.g. pathological or physiological features) that can vary in size, appearance, texture or the like, it is desired to improve the performance of a machine learning model, such as a neural network, in order to provide a highly accurate segmentation or classification for the various different types of medical features such as pathological or physiological features, especially for distinct sub-tasks that are underrepresented in the medical images used for training a general machine learning model. This disclosure relates to an improved technique aimed at addressing the limitations associated with existing techniques.

Briefly, there is described herein a computer implemented method for medical image processing. The method comprises providing a database of medical images and providing an initial machine learning model which is trained for segmenting or classifying a medical feature in the medical images. The method also comprises extracting a subset of medical images from the database based on a similarity score of the medical images and training the machine learning model using the extracted subset of medical images in order to provide a refined (or fine-tuned) machine learning model.

Herein, a medical feature (or characteristic) may comprise any feature in a medical image that can be used in identifying or characterizing a medical condition. Examples of a medical feature include, but are not limited to, a pathological feature, a physiological feature, or any other medical feature, or any combination of medical features. A pathological feature (or characteristic) can be defined as any feature in a medical image that can be used in identifying or characterizing a pathological condition (e.g. a disease). An example of a pathological feature is a tumor. A physiological feature can be defined as any feature (or characteristic) in a medical image that can be used in identifying or characterizing a physiological condition (e.g. the condition of the body or bodily functions). An example of a physiological feature is an inflammation.

Any references to "identifying a medical feature" herein will be understood to cover both the task of segmenting a medical feature and the task of classifying a medical feature. The references to "segmenting a medical feature" herein will be understood to mean detecting a medical feature in a medical image and, more specifically, may comprise detecting a location of the medical feature in the medical image and/or one or more boundaries of the medical feature in the medical image. The references to "classifying a medical feature" herein will be understood to mean assigning the medical feature to a class (or category), e.g. evaluating the medical feature according to a predetermined classification system.

Figure 1:
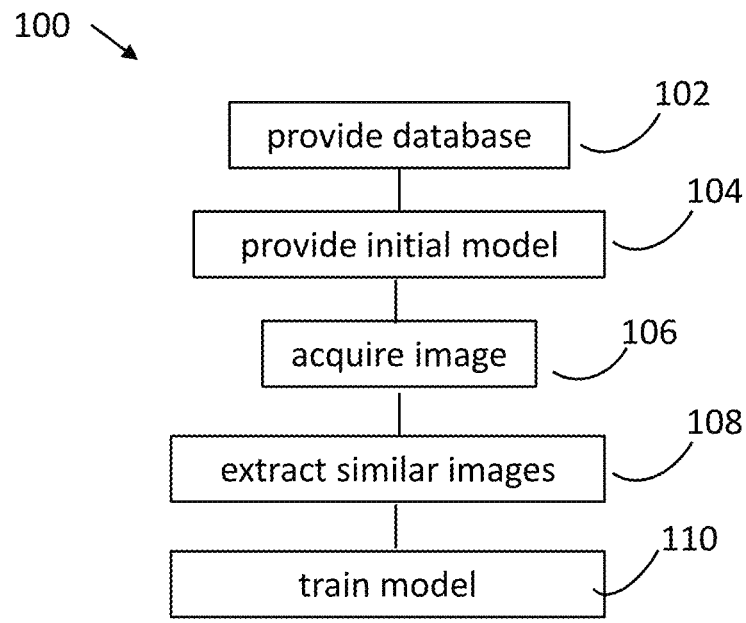
FIG. 1 shows a flowchart of an example computer implemented method according to a first embodiment that uses on-line network refinement.

FIG. 1 shows a computer implemented method 100 for medical image processing according to a first embodiment, wherein a database of medical images is provided in block 102. The medical images referred to herein may comprise any type of medical images, e.g. computerized tomography (CT) scans, magnetic resonance imaging (MRI) images, X-ray images or the like, and may depict any medical structure such as organs, bones, fetuses, or the like. An initial machine learning model is provided in block 104, wherein the initial machine learning model is trained for segmenting or classifying a medical feature in the medical images. For example, the initial machine learning model may have been trained using the medical images in the database for segmentation or classification of a medical feature. Herein, the initial machine learning model may be any type of machine learning model, e.g. a neural network model or any other type of machine learning model.

A medical image that is to be processed is acquired in block 106 and a subset of medical images are extracted from the database at block 108 based on a similarity score of the medical images. In the illustrated embodiment of FIG. 1, the step of extracting the subset of medical images from the database in block 108 is performed based on a similarity score between the acquired medical image and the extracted medical images. Thus, a subset of similar medical images to the acquired image are identified in the database in block 108.

Although not illustrated in FIG. 1, in some embodiments, the method may comprise identifying a region of interest in the acquired medical image, and determining the similarity score based on the region of interest. In some embodiments, the similarity score may be determined based on content information of the medical images and/or based on a latent space representation of the medical images in the database. In more detail, for example, the similarity of a medical image in the database to the acquired image may be determined by means of image retrieval, wherein a similarity score may be determined by learning a latent space representation A of the training images, such that similar images (according to a given similarity measure, e.g. sum of squared differences, SSD) have a small Euclidean distance in A. Finding images similar to the acquired image can then be efficiently determined by mapping the acquired image to the latent space. Therein, a region of interest, ROI, may be identified in the acquired image and the similarity score may be determined based on the region of interest in order to ensure that the medical images in the subset are selected based on similar medical features (e.g. physiologies or pathologies), instead of e.g. being erroneously selected based one similar scan artefacts or similar features relating to background portions of the acquired image.

In block 110, the machine learning model is trained using the extracted subset of medical images in order to provide a refined machine learning model. More specifically, once a suitable subset of similar medical images has been identified, the initial machine learning model can be trained on the subset in order to improve the model's performance for the specific medical feature, appearance or task represented by the selected subset. Thus, a refined machine learning model can be provided that comprises the initial model's capabilities as trained on the complete database of medical images, as well as being fine-tuned to the task of accurately segmenting or classifying a medical feature in a specific acquired image.

Although not illustrated in FIG. 1, in some embodiments, the method may comprise processing the acquired medical image using the refined machine learning model, e.g. in order to provide a processing result of the acquired medical image. For example, the method may comprise segmenting or classifying a medical feature in the acquired medical image using the refined machine learning model. That is, the acquired medical image may be processed using the refined machine learning model to identify (e.g. segment or classify) a medical feature in the acquired medical image. Thus, the method according to the first embodiment describes an approach to fine-tune a general machine learning model (e.g. a neural network model) to a specific segmentation or classification (sub-) task via transfer learning.

The main concept of transfer learning is that a first (i.e. the initial model) is trained on a general task for which a large amount of training data is available. Then, the trained model (including the learned features, which are useful to solve the general task) is adapted or refined to perform a second, related task, for which typically much less training data is available. Hence, the refined machine learning model builds upon and only fine-tunes powerful features of a more general model instead of learning new features from scratch on small data sets. In the presently described embodiments, the method can intelligently select a suitable subset of training images for model-refinement. In contrast to this, classical transfer learning usually comprises a separate and predetermined training set for refining the general model.

Figure 2:
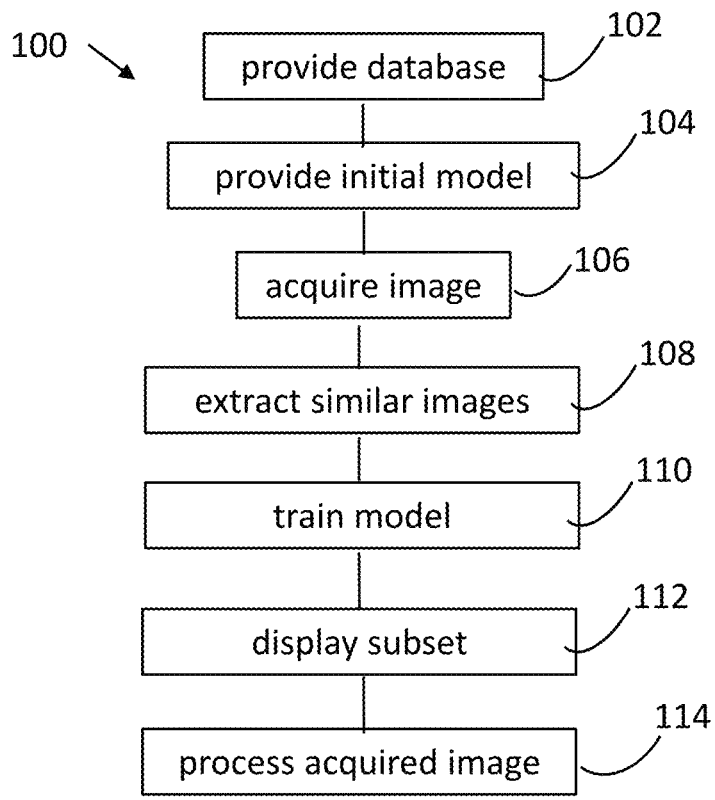
FIG. 2 shows a modified method according to the first embodiment.

FIG. 2 shows a modified method 100 according to the first embodiment, wherein, in addition to blocks 102 to 110 described above in conjunction with FIG. 1, the extracted subset of medical images may optionally be displayed (e.g. to a clinician) in block 112. This can allow the clinician to review whether the refined machine learning model has been trained based on suitable training images that e.g. show the same type or the same appearance of a medical feature. The acquired medical image may be processed (e.g. analyzed) in block 114, using the refined machine learning model, e.g. in order to provide a processing result of the acquired medical image. For example, in block 114, the acquired medical image may be processed using the refined machine learning model to identify (e.g. segment or classify) a medical feature in the acquired medical image.

Figure 3:
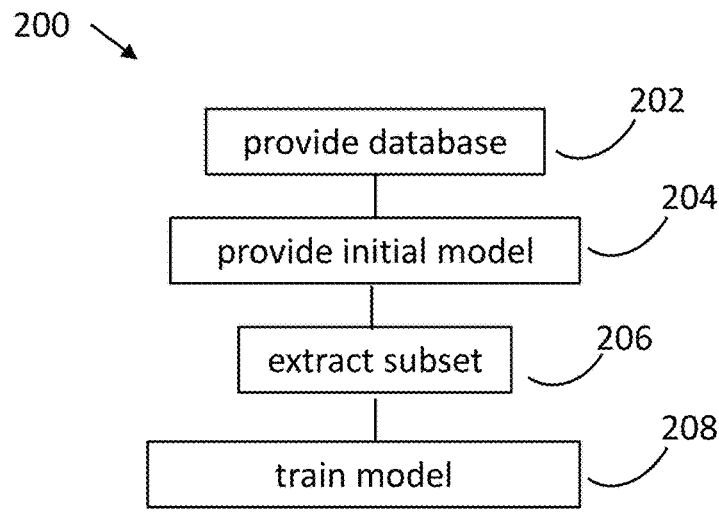
FIG. 3 shows a flowchart of an example computer-implemented method according to a second embodiment that uses off-line network refinement.

FIG. 3 illustrates a computer implemented method 200 for medical image processing according to a second embodiment, wherein a database of medical images is provided in block 202. As mentioned earlier, the medical images referred to herein may comprise any type of medical images, e.g. CT scans, MRI images, X-ray images or the like, and may depict any medical structure such as organs, bones, fetuses, or the like. An initial machine learning model is provided in block 204, wherein the initial machine learning model is trained for segmenting or classifying a medical feature in the medical images. For example, the initial machine learning model may have been trained using the medical images in the database, e.g. for segmentation or classification of a medical feature (e.g. a pathological or physiological feature). For example, the initial machine learning model may have been trained for segmentation of a fetus in an ultrasound image, or the like. As mentioned earlier, herein, the initial machine learning model may be any type of machine learning model, e.g. a neural network model or any other type of machine learning model.

In block 206, a subset of medical images is extracted from the database based on a similarity score of the medical images. In some embodiments, the similarity score may be determined based on content information of the medical images and/or based on a latent space representation of the medical images in the database. For example, a subset of medical images in the database may be identified by clustering the medical images in latent space A and by identifying a subset as a specific cluster using a suitable granularity. Clustering can either be done solely based on the latent space representation (e.g., using the k-means algorithm), or incorporating additional content information of the medical images, e.g. the nodule type, size, degree of spiculation. In block 208, the machine learning model is trained using the extracted subset of medical images in order to provide a refined machine learning model. That is, the initial model is refined for the selected cluster/subset in block 208.

Thus, a refined machine learning model can be provided for a particular cluster of medical images, which can then be used to process similar images to those images contained in the cluster at a higher accuracy than can be achieved with the general, initial model. Compared to the first embodiment, the second embodiment achieves a reduction of computation time at the expense of a case-specific model.

In some embodiments, in block 206, multiple subsets of medical images may be extracted from the database based on a similarity score between the medical images of the database. In some of these embodiments, the method may also comprise acquiring a medical image and selecting one subset of the multiple extracted subsets of medical images based on a similarity score between the medical images in each of the extracted subsets and the acquired medical image. Thus, in these embodiments, the method can comprise segmenting or classifying a medical feature in the acquired medical image using the refined machine learning model which has been trained using the selected subset of medical images.

Although not illustrated in FIG. 3, in some embodiments, the method may comprise processing the acquired medical image using the refined machine learning model, e.g. in order to provide a processing result of the acquired medical image. For example, the method may comprise segmenting or classifying a medical feature in the acquired medical image using the refined machine learning model. That is, the acquired medical image may be processed using the refined machine learning model to identify (e.g. segment or classify) a medical feature in the acquired medical image.

Figure 4:
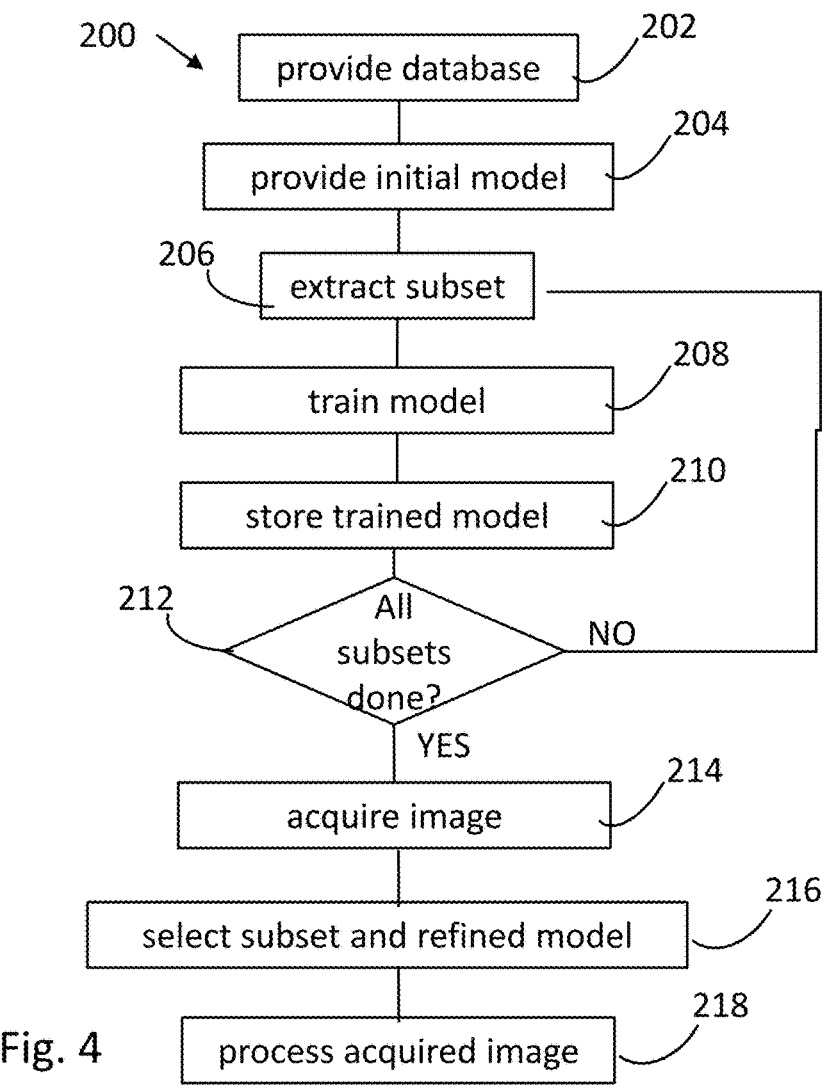
FIG. 4 shows a modified method according to the second embodiment.

FIG. 4 shows a modified method 200 of the second embodiment, wherein, in addition to blocks 202 to 208 described above in conjunction with FIG. 3, a trained refined machine learning model for a subset of medical images may be stored in block 210. It may be determined in block 212 whether all subsets (e.g. clusters) of medical images as defined in block 206 have yet been processed. If the answer is "NO" (i.e. if all subsets of medical images have not been processed), processing returns to block 206 at which a different subset of medical images may be extracted from the database in the manner described earlier and, in block 208, the initial machine learning model may be trained using the medical images of the different subset (e.g. cluster), until a respective machine learning model has been trained for all subsets (e.g. clusters) so that, for each subset (e.g. cluster) of medical images, a refined machine learning model is provided and can be stored in block 210. Thus, in the embodiment illustrated in FIG. 4, multiple subsets of medical images may be extracted from the database based on a similarity score between the medical images of the database.

Once all subsets (e.g. clusters) of medical images have been processed in this manner ("YES" in block 212), an image to be processed may be acquired in block 214. In block 216, one subset of the multiple extracted subsets of medical images is selected based on a similarity score between the medical images in each of the extracted subsets and the acquired medical image. For example, using a similarity score as described in conjunction with block 108 of the first embodiment, the subset (e.g. cluster) which has the greatest similarity to the acquired image may be selected in block 216. The corresponding refined machine learning model for the selected subset (e.g. cluster) may also be retrieved in block 216. The acquired medical image may be processed (e.g. analyzed) in block 218, using the retrieved refined machine learning model, e.g. in order to provide a processing result of the acquired medical image. For example, the acquired medical image may be processed in block 218, using the retrieved refined machine learning model, in order to identify (e.g. segment or classify) a medical feature in the acquired medical image.

Thus, with the method according to the second embodiment, once an image has been acquired, processing can be performed in a fast manner, since the training of the refined machine learning model has already been performed previously on the subsets (e.g. clusters) of medical images in the database. However, the refined machine learning models of the second embodiment are not trained specifically for an acquired image, but are trained according to the subset (e.g. cluster) structure of the medical images in the database.

Figure 5:
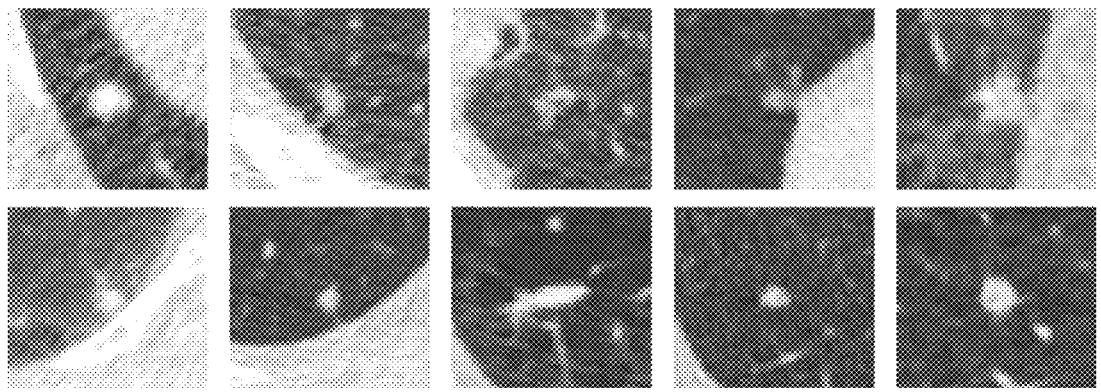
FIG. 5 shows examples of medical images that may be used for the methods according to the embodiments.

FIG. 5 shows an example of the type of medical images that may be used in embodiments of the present disclosure. The medical images shown in FIG. 5 are examples for the huge variety possible appearances of lung nodules as shown in CT scan images. For example, the database may comprise solid, part-solid and/or non-solid nodules of different sizes and with different borders. As can be seen from the individual images shown in FIG. 5, providing a medical feature segmentation or classification based on such a large range of different shapes, sizes and appearances may lead to specific cases being wrongly segmented or classified. Therefore, fine-tuning features to a specific sub-task is potentially superior to learning generic features for all possible appearances.

Using the medical images exemplified in FIG. 5, a suitable machine learning model, such as a (convolutional) neural network, may be trained for the task of feature segmentation (for example, nodule segmentation) or classification. An initial segmentation or classification model may be trained using all images of the database.

According to further examples, ultrasound images of fetuses may be used, wherein the appearance of fetuses may also be very heterogeneous due to different positions of the baby in the womb and different sizes and developmental stages of the fetus.

Figure 6A:
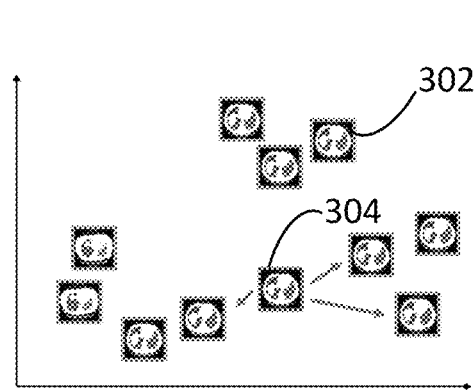
FIGS. 6A and 6B show a comparison of on-line and off-line network refinement.
Figure 6B:
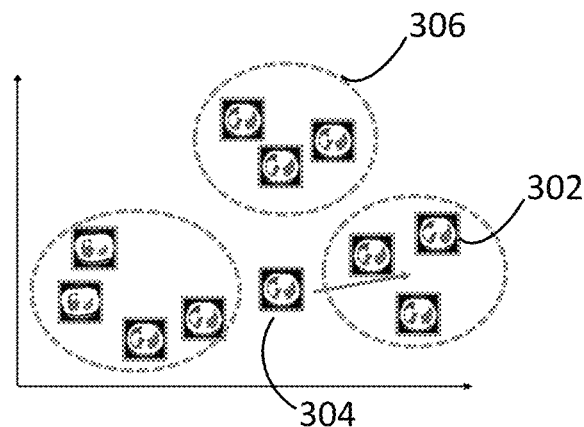

FIGS. 6A and 6B illustrate some of the differences between the first and second embodiments described above. FIG. 6A shows a method of on-line model refinement according to the first embodiment in which, of the medical images 302 stored in the database, a number of similar images may be selected based e.g. on a distance of the acquired image 304 to the selected images in latent space, and a refined machine learning model can then be trained on-demand. Here, fine-tuning implies additional computational cost but yields a refined machine learning model for the segmentation or classification task at hand.

FIG. 6B shows a method of off-line model refinement according to the second embodiment in which training medical images 302 are first clustered in the latent space and a refined machine learning model is learned for each cluster 306. When an image 304 is acquired for processing, it is analyzed using the refined machine learning model that corresponds to the most similar cluster 306.

In analyzing acquired medical images according to the above-described method, a region of interest (ROI) around the medical feature may be chosen, which may then be used to define the embedding, i.e. to evaluate and compare the respective similarity scores between the acquired medical image and the medical images in the database. This allows appropriate training data to be retrieved on a per-feature-basis, in contrast to a per-scan-basis. For the on-line refinement approach, the most similar cases for the ROI may be searched via the latent space embedding and the segmentation or classification model may be refined using these cases and applied to the ROI. For the off-line learning approach according to the second embodiment, the nearest cluster in the latent space may be retrieved and the corresponding specialized model may be used for segmentation or classification.

In order to increase confidence for the system described herein, the images selected for network refinement may be displayed, e.g. to the clinician (for example, it may be displayed that a nodule was determined to be ground glass and the corresponding module has been selected as a result). Since the variation in cases that may need to be searched for may be very large, an appropriate result will likely not be stored locally on the clinician's workstation, but an online-retrieval may be necessary.

Figure 7:
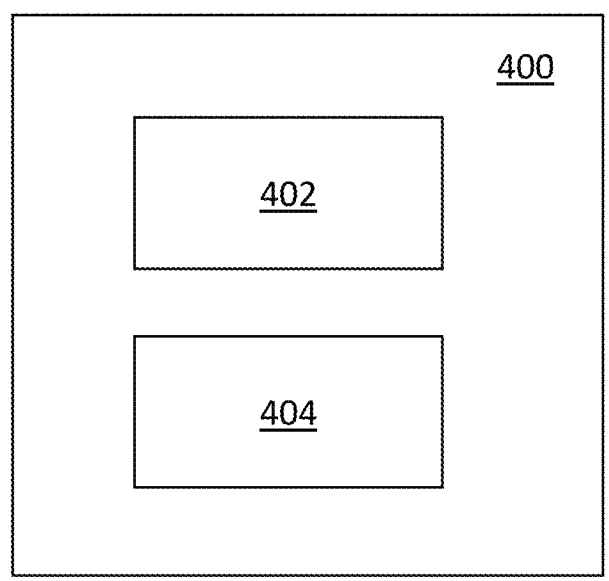
FIG. 7 illustrates an example system for medical image processing system according to embodiments.

FIG. 7 is a schematic illustration of a system 400 comprising a memory 402 for storing the database of medical images described herein and a processor 404 for performing a method according to any of the embodiments described herein.

Various network architectures have been proposed for image classification or image segmentation—often referred to as semantic segmentation—and the embodiments described herein are independent from a specific approach. The methods according to all of the embodiments described above can retrieve similar images by means of intelligent selection algorithms and using these for training more refined (or specific) machine learning models. This enables fine-tuning of an initially trained, general machine learning model based on a subset of the original database, which is a central differentiator from common transfer learning approaches. To learn the latent space representation A that may be used according to some embodiments, several methods can be used, for example manifold-learning or auto-encoders.

Figure 8:
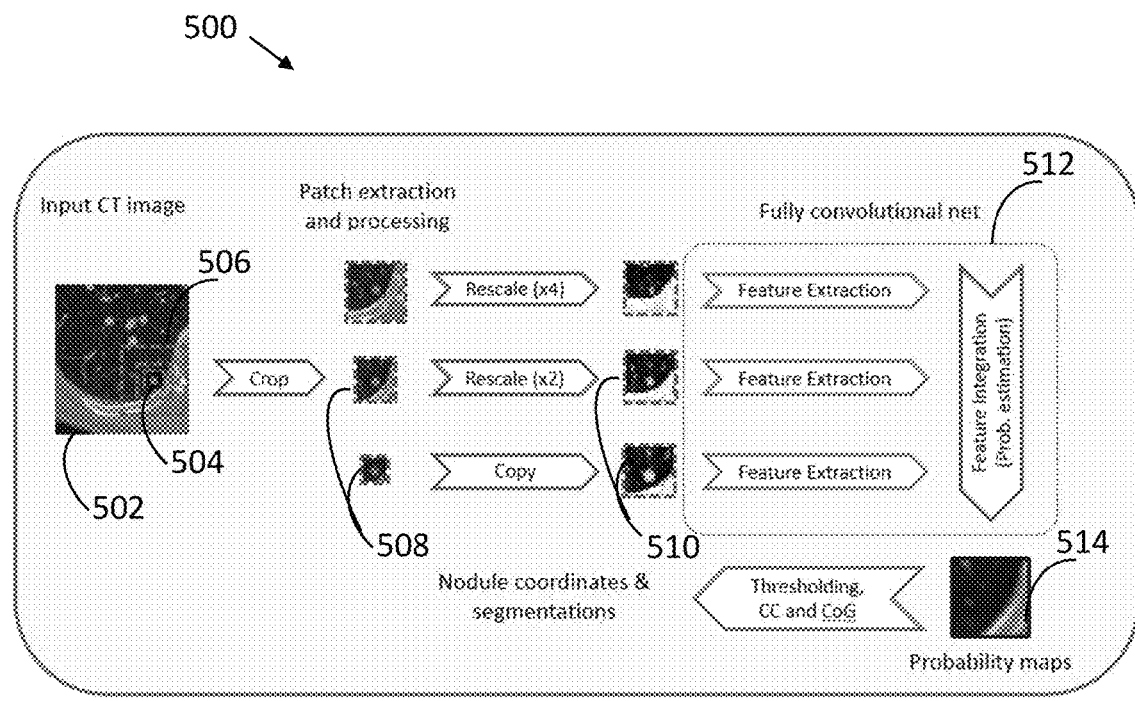
FIG. 8 shows an example architecture for a first neural network system that may be employed for the methods according to the embodiments.

FIG. 8 shows a first example of a network architecture for a machine learning model 500 which may be employed in embodiments of the online and offline model refinement methods as described above.

Prior to the processing as shown in FIG. 8, the machine learning model 500 has received training based on a database of medical images. In the present example, it is assumed that the machine learning model 500 of FIG. 8 corresponds to the refined machine learning model as described above, which has first been trained using a large set of available medical images, and has subsequently received further training based on a selected smaller subset of medical images that are particularly relevant for a specific subtask, as described above, using either the online or the offline refinement process as shown in FIG. 6.

The machine learning model 500 comprises an input section wherein a medical image 502, such as a CT image, may be initially processed in order to identify a region of interest (ROI) 504. In this example, the ROI may be formed of a frame of a predetermined size, which may be moved along the medical image 502 in order to ensure that each region of the medical image 502 is processed. The ROI 504 may further be used to determine a similarity score in order to select a suitable subset of training images for online model refinement, as described above (not shown in FIG. 8), or for selecting a suitable refined model from a plurality of refined models based on different subsets of training images (not shown in FIG. 8).

Subsequently, multiple patch frames 506 of different sizes may be defined, wherein each patch frame 506 includes the ROI 506. In a subsequent patch extraction and processing section, the original medical image 502 may be cropped so as to yield multiple patch images 508. The patch images 508 may then be processed by copying and rescaling so as to yield processed patch images 510 of different resolutions that can be input into a fully convolutional neural network 512, wherein feature extraction processing may be performed. Therein, the use of patch images at different resolutions ensures that resolution-related artefacts can be avoided and that medical features depicted in the respective ROI 504 can be extracted with high accuracy. The neural network 512 may output a resulting image 514 which may comprise a probability map that can then subsequently used for segmentation of a specific medical feature. The segmentation processing may use threshold-based analyses of the resulting images, as well as further analyses, such as e.g. "Connected Components" (CC) analysis, which is usually applied to determine connected regions (i.e., segments that correspond to individual objects/nodules) after the thresholding of probabilities. In order to obtain the position of a nodule, a center of gravity (CoG) may be calculated in order to determine presence or absence and the outline of the medical feature such as a lung nodule or the like.

As discussed above, since the machine learning model 500 as shown in FIG. 8 has been subjected to additional training in order to arrive at a refined machine learning model 500 for a specific sub-task, it can achieve an accurate segmentation result of the medical feature even if the input medical image corresponds to a specific subtask that may have been underrepresented in the general database of training images.

Figure 9:
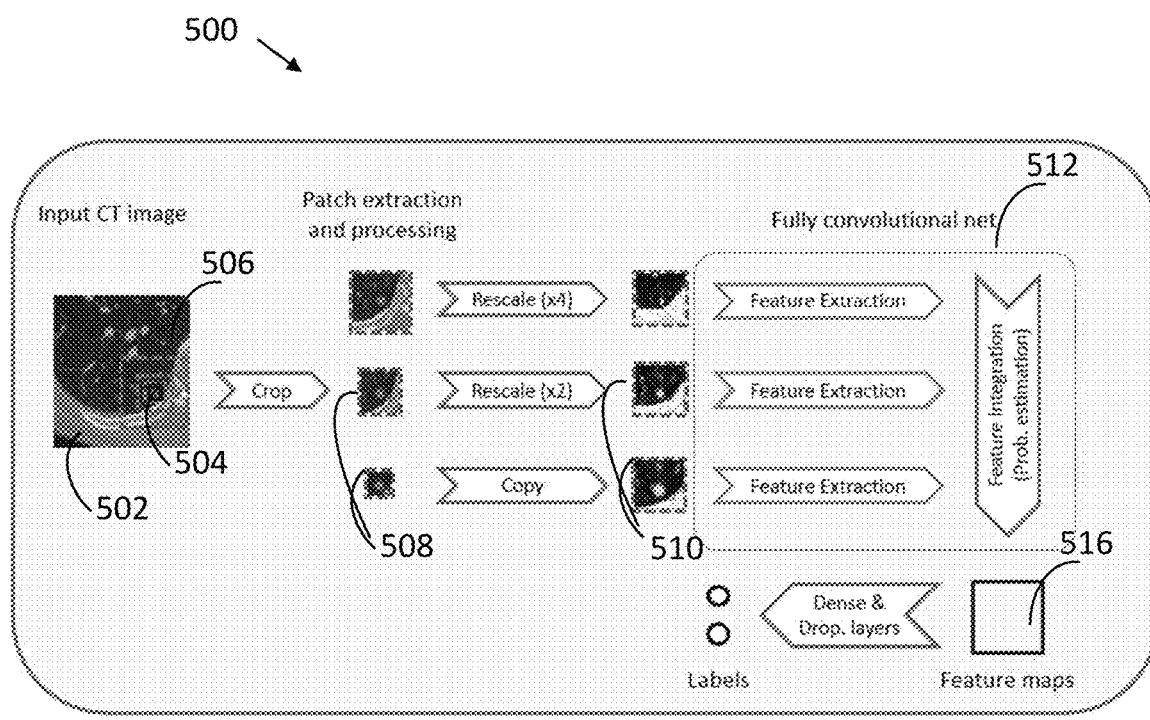
FIG. 9 shows an example architecture of a further neural network system that may be employed for the methods according to the embodiments.

The machine learning model 500 of FIG. 8 is directed specifically at segmentation tasks. However, as shown in FIG. 9, an alternative machine learning model 500 with a very similar structure may be employed for classification tasks. Similar to the description of the processing using the machine learning model 500 of FIG. 8 above, the machine learning model 500 of FIG. 9 may be a refined machine learning model that has been previously trained using first a large number of medical images provided in a database, and that has subsequently received additional training based on a selected subset of training images from the database based on the similarity of a ROI 504 on an input medical image 502 to respective medical images in the training database.

Therein, as described above in conjunction with FIG. 8, a medical image 502, such as a CT image, may be processed by defining a ROI 504 and suitable patch frames 506. For classification tasks, the machine learning model may make use of a prior segmentation processing, wherein a ROI may be defined around a previously-segmented medical (e.g. pathological or physiological) feature. The patch images 508 are extracted and rescaled, so that processed patch images 510 of different resolutions can be input into the fully convolutional neural network 512. The output of the neural network 512 for the classification machine learning model 500 may be presented as a feature map image 516 which may be processed further in order to provide a classification result wherein a given medical image may be labelled according to a predetermined classification system. For classification, one or multiple densely connected layers may be provided at the end of the network to reduce the feature maps to just N neurons, with N being the number of classes of the classification task. To enhance the robustness and ability to generalize of the approach, drop layers may be added between two dense layers.

Therein, similar to the segmentation machine-learning model 500 as described above, the online or offline model refinement methods according to the embodiments described in conjunction with FIGS. 1-6 may be employed in order to obtain a refined machine learning model 500 for classification of a particular subtask or of a particular acquired medical image.

The above-described embodiments provide effective and accurate methods and systems for the segmentation or classification of all kinds of medical features (e.g. physiological features or pathological features, like tumors or lung nodules) from acquired medical images using a machine learning model which has been refined using a subset of training medical images that are chosen based on a similarity score of the medical images, e.g. which are similar to the acquired image that is being analyzed. The same approach may also be beneficial for segmenting or classifying other medical features (e.g. structures) with large anatomical variance, such as lymph nodes, bone fractures or images of fetuses. The above-described methods and concepts may even be applied to non-medical images, such as face recognition in images or the like.

There is also provided a computer program product comprising a computer readable medium, the computer readable medium having computer readable code embodied therein, the computer readable code being configured such that, on execution by a suitable computer or processor, the computer or processor is caused to perform the method or methods described herein. Thus, it will be appreciated that the invention also applies to computer programs, particularly computer programs on or in a carrier, adapted to put the invention into practice. The program may be in the form of a source code, an object code, a code intermediate source and an object code such as in a partially compiled form, or in any other form suitable for use in the implementation of the method according to the invention.

It will also be appreciated that such a program may have many different architectural designs. For example, a program code implementing the functionality of the method or system according to the invention may be sub-divided into one or more sub-routines. Many different ways of distributing the functionality among these sub-routines will be apparent to the skilled person. The sub-routines may be stored together in one executable file to form a self-contained program. Such an executable file may comprise computer-executable instructions, for example, processor instructions and/or interpreter instructions (e.g. Java interpreter instructions). Alternatively, one or more or all of the sub-routines may be stored in at least one external library file and linked with a main program either statically or dynamically, e.g. at run-time. The main program contains at least one call to at least one of the sub-routines. The sub-routines may also comprise function calls to each other.

An embodiment relating to a computer program product comprises computer-executable instructions corresponding to each processing stage of at least one of the methods set forth herein. These instructions may be sub-divided into sub-routines and/or stored in one or more files that may be linked statically or dynamically. Another embodiment relating to a computer program product comprises computer-executable instructions corresponding to each means of at least one of the systems and/or products set forth herein. These instructions may be sub-divided into sub-routines and/or stored in one or more files that may be linked statically or dynamically.

The carrier of a computer program may be any entity or device capable of carrying the program. For example, the carrier may include a data storage, such as a ROM, for example, a CD ROM or a semiconductor ROM, or a magnetic recording medium, for example, a hard disk. Furthermore, the carrier may be a transmissible carrier such as an electric or optical signal, which may be conveyed via electric or optical cable or by radio or other means. When the program is embodied in such a signal, the carrier may be constituted by such a cable or other device or means. Alternatively, the carrier may be an integrated circuit in which the program is embedded, the integrated circuit being adapted to perform, or used in the performance of, the relevant method.

Variations to the disclosed embodiments can be understood and effected by those skilled in the art in practicing the principles and techniques described herein, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored or distributed on a suitable medium, such as an optical storage medium or a solid-state

The invention claimed is:

1. A computer implemented method for medical image processing, comprising:
   providing a database of medical images;
   providing an initial machine learning model which is trained for segmenting or classifying a medical feature in the medical images;
   extracting a subset of medical images from the database based on a similarity score of the medical images;
   training the machine learning model using the extracted subset of medical images in order to provide a refined machine learning model;
   extracting multiple subsets of medical images from the database based on a similarity score between the medical images of the database;
   acquiring a medical image;
   selecting one subset of the multiple extracted subsets of medical images based on a similarity score between the medical images in each of the extracted subsets and the acquired medical image; and
   segmenting or classifying a medical feature in the acquired medical image using the refined machine learning model which has been trained using the selected subset of medical images.

2. The method according to claim 1, further comprising:
   acquiring a medical image that is to be processed,
   wherein the step of extracting the subset of medical images from the database is performed based on a similarity score between the acquired medical image and the extracted medical images.

3. The method according to claim 2, further comprising:
   identifying a region of interest in the acquired medical image, and determining the similarity score based on the region of interest.

4. The method according to claim 2, further comprising:
   segmenting or classifying a medical feature in the acquired medical image using the refined machine learning model.

5. The method according to claim 1, wherein the initial machine learning model is trained for feature segmentation or classification using the database of medical images.

6. The method according to claim 1, wherein the medical images comprise any of computerized tomography scan images, X-ray images, or magnetic resonance imaging images.

7. The method according to claim 1, wherein the similarity score is determined based on a latent space representation of the medical images in the database.

8. The method according to claim 1, wherein the similarity score is based on content information of the medical images.

9. The method according to claim 1, further comprising:
   displaying the extracted subset of medical images.

10. A system for medical image processing, comprising:
    a memory storing a database of medical images;
    a processor configured to:
       provide an initial machine learning model which is trained for segmenting or classifying a medical feature in the medical images;
       extract a subset of medical images from the database based on a similarity score of the medical images;
       train the machine learning model using the extracted subset of medical images in order to provide a refined machine learning model;
       extract multiple subsets of medical images from the database based on a similarity score between the medical images of the database;
       acquire a medical image;
       select one subset of the multiple extracted subsets of medical images based on a similarity score between the medical images in each of the extracted subsets and the acquired medical image; and
       segment or classify a medical feature in the acquired medical image using the refined machine learning model which has been trained using the selected subset of medical images.

11. A non-transitory computer readable medium storing computer readable instructions that, when executed by one or more processors, cause the one or more processors to:
    access an initial machine learning model which is trained for segmenting or classifying a medical feature in medical images;
    extract a subset of medical images from a database of medical images based on a similarity score of the medical images;
    train the machine learning model using the extracted subset of medical images in order to provide a refined machine learning model;
    extract multiple subsets of medical images from the database based on a similarity score between the medical images of the database;
    acquire a medical image;
    select one subset of the multiple extracted subsets of medical images based on a similarity score between the medical images in each of the extracted subsets and the acquired medical image; and
    segment or classify a medical feature in the acquired medical image using the refined machine learning model which has been trained using the selected subset of medical images.

* * * * *